(12) United States Patent
Bond et al.

(10) Patent No.: US 9,556,224 B2
(45) Date of Patent: Jan. 31, 2017

(54) ANTIMICROBIAL COMPOSITIONS AND METHODS OF USE THEREOF

(71) Applicant: MOREHOUSE SCHOOL OF MEDICINE, Atlanta, GA (US)

(72) Inventors: Vincent Craig Bond, Stone Mountain, GA (US); Michael Powell, Douglasville, GA (US); Ming Bo Huang, Atlanta, GA (US); Syed Ali, Pulau Pinang (MY); Martin Neville Shelton, Stone Mountain, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 0 days.

(21) Appl. No.: 14/156,119

(22) Filed: Jan. 15, 2014

(65) Prior Publication Data
US 2014/0155319 A1   Jun. 5, 2014

Related U.S. Application Data

(63) Continuation of application No. 13/267,977, filed on Oct. 7, 2011, now Pat. No. 8,669,226.

(51) Int. Cl.
*C07K 7/06* (2006.01)
*A61K 38/08* (2006.01)

(52) U.S. Cl.
CPC ........ *C07K 7/06* (2013.01); *A61K 38/08* (2013.01)

(58) Field of Classification Search
None
See application file for complete search history.

(56) References Cited

U.S. PATENT DOCUMENTS

| | | | |
|---|---|---|---|
| 8,431,530 B2 | 4/2013 | Bond et al. | |
| 8,476,237 B2 | 7/2013 | Bond et al. | |
| 8,551,943 B2 | 10/2013 | Bond et al. | |
| 8,563,506 B2 | 10/2013 | Bond et al. | |
| 8,669,226 B2 * | 3/2014 | Bond et al. | 514/2.8 |
| 2006/0140911 A1 | 6/2006 | Sharp et al. | |
| 2007/0055049 A1 * | 3/2007 | Grey et al. | 530/350 |
| 2008/0057038 A1 | 3/2008 | Yacoby et al. | |
| 2010/0061932 A1 | 3/2010 | Brock et al. | |
| 2010/0317566 A1 * | 12/2010 | Bond et al. | 514/3.7 |
| 2010/0322929 A1 | 12/2010 | Zurawski et al. | |
| 2011/0020290 A1 | 1/2011 | Soothill et al. | |
| 2011/0046008 A1 | 2/2011 | Love et al. | |
| 2013/0018002 A1 | 1/2013 | Bond et al. | |
| 2013/0018003 A1 | 1/2013 | Bond et al. | |
| 2013/0123202 A1 | 5/2013 | Bond et al. | |
| 2014/0155319 A1 * | 6/2014 | Bond et al. | 514/2.6 |

FOREIGN PATENT DOCUMENTS

WO   PCT/US2011/055219   10/2011

OTHER PUBLICATIONS http://en.wikipedia.org/wiki/Polymyxin, last updated Oct. 26, 2014.*
Morris, et al., "A Peptide Carrier for the Delivery of Biologically Active Proteins into Mammalian Cells: Application to the Delivery of Antibodies and Therapeutic Proteins", Nature Biotechnology, vol. 19, pp. 1173-1176 (2001).
Joliot, et al., "Transduction peptides: from technology to physiology", Nature Cell Biology, vol. 6, No. 3, pp. 189-196 (2004).
Heitz, et al., "Twenty years of cell-penetrating peptides: from molecular mechanisms to therapeutics", British Journal of Pharmacology, vol. 157, pp. 195-206 (2009).
Yacoby, et al., "Targeting Antibacterial Agents by Using Drug-Carrying Filamentous Bacteriophages", Antimicrobial Agents and Chemotherapy (AAC), vol. 50, No. 6, pp. 2087-2097 (2006).
Yacoby, et al. "Targeted Drug-Carrying Bacteriophages as Antibacterial Nanomedicines", Antimicrobial Agents and Chemotherapy (AAC), vol. 51, No. 6, pp. 2156-2163 (2007).
Proft, "Sortase-mediated protein ligation: an emerging biotechnology tool for protein modification and immobilisation", Biotechnol Lett, vol. 32, pp. 1-10 (2010).
Ali, S.A., et al., "Genetic Characterization of HIV Type 1 Nef-Induced Vesicle Secretion", AIDS Research and Human Retroviruses, vol. 26, No. 2, pp. 173-192 (2010).
International Search Report and Written Opinion of the International Searching Authority, mailed May 25, 2012 (Application No. PCT/US2011/055219, filed Oct. 7, 2011).
U.S. Appl. No. 13/267,977, filed Oct. 7, 2011, Pending.

* cited by examiner

*Primary Examiner* — Maury Audet
(74) *Attorney, Agent, or Firm* — Ping Wang; Andrews Kurth Kenyon LLP (57) ABSTRACT

The present application discloses a method for treating microbial infection using an antimicrobial composition comprises antimicrobial peptide which contains at least one VGFPV motif.

10 Claims, 7 Drawing Sheets

ANTIMICROBIAL COMPOSITIONS AND METHODS OF USE THEREOF

This application is a Continuation of U.S. application Ser. No. 13/267,977, filed Oct. 7, 2011. The entirety of the aforementioned application is incorporated herein by reference.

FIELD

The present application relates generally to compositions and method for medical treatment and, in particular, to antimicrobial compositions and method for treating microbial infections.

BACKGROUND

Multidrug resistant microorganisms have become a major health concern worldwide. The multidrug resistance bacteria are generally divided into four groups, MRSA (methicillin/oxacillin-resistant *Staphylococcus aureus*). VRE (vancomycin-resistant *enterococci*), ESBLs (extended-spectrum beta-lactamases), and PRSP (penicillin-resistant *Streptococcus pneumonia*). Multidrug resistant bacteria are becoming increasingly problematic, particularly in health care and hospital settings.

Most organisms produce gene encoded antimicrobial peptides (AMPs) as innate defenses to prevent colonization and infection by multiple microbial pathogens. As such, AMPs are nature's antibiotics and have been the subject of intense research development, particularly against drug resistant microorganisms. AMPs have varying microbial specificities, cellular targets, modes of action, potencies, and adverse side effects against mammalian cells. Many of the AMPs under development suffer from weak activity, nonspecific cytotoxicity, and susceptibility to proteolysis. Accordingly, there is a need for new and effective AMPs, particularly for use against multiple drug resistant pathogens.

SUMMARY

One aspect of the present invention relates to a Method of treating a microbial infection by administering to a subject in need thereof an effective amount of an antimicrobial peptide comprising a first antimicrobial domain comprising at least one VGFPV (SEQ ID NO:1) motif.

Figure 8:
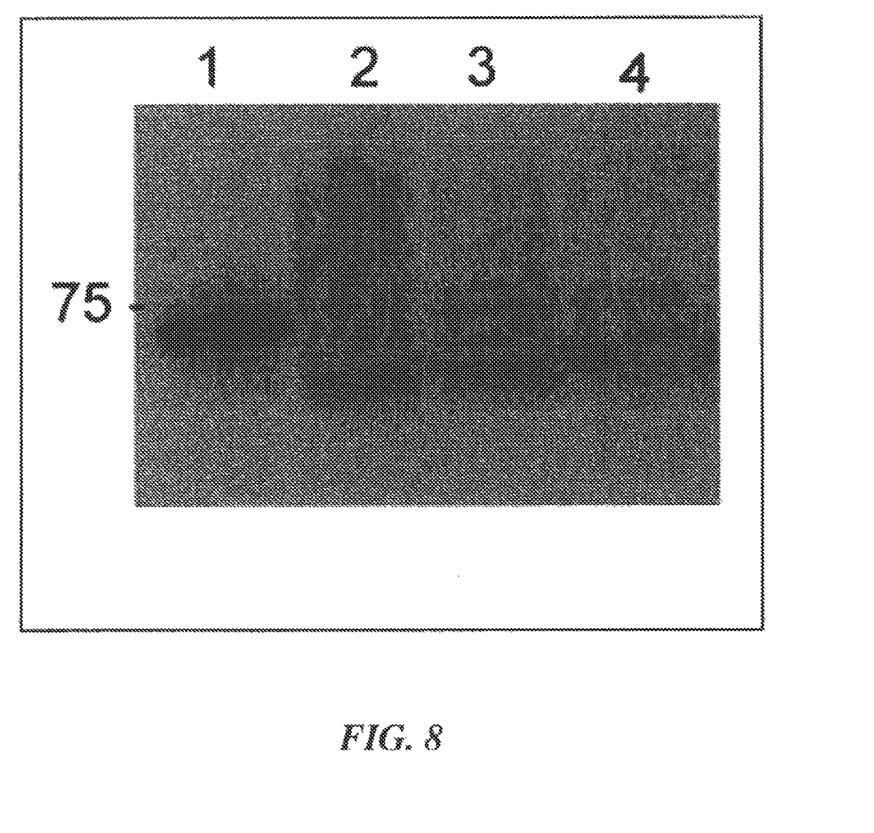

Another aspect of the present invention relates to a method of treating a microbial infection by administering to a subject in need of such treatment an effective amount of an in vivo expression vector that encodes an antimicrobial peptide comprising a first antimicrobial domain comprising at least one VGFPV (SEQ ID NO: 1) motif.

Another aspect of the present invention relates to a method of treating a microbial infection by administering to a subject in need of such treatment an effective amount of a bacteriophage displaying an antimicrobial peptide on its surface. The antimicrobial peptide comprises a first antimicrobial domain comprising at least one VGFPV (SEQ ID NO: 1) motif. Another aspect of the present invention relates to a pharmaceutical composition for treating microbial infection. The pharmaceutical composition comprises (1) an antimicrobial peptide comprising a first antimicrobial domain comprising at least one VGFPV (SEQ ID NO:1) motif, and a CCP domain and/or targeting domain; and (2) a pharmaceutically acceptable carrier.

BRIEF DESCRIPTION OF DRAWINGS

FIG. 1 is a composite of diagrams showing a synthetic HIV-1 Nef SMRwt peptide (SEQ ID NO: 5, antibacterial peptide) and HIV-1 Nef SMRmut peptide (SEQ ID NO:7, negative control) (panel A); the vector constructs expressing HIV-1 Nef SMRwt peptide fused with GFP or HIV-1 Nef SMRmut peptide fused with GFP (panel B). In both synthetic peptide and vector, the SMRwt or SMRmut sequences are identical. There are two SMR motifs in the synthetic peptides while only one in the vector constructs. Arrows show site of amino acid changes in SMRmut motifs.

FIG. 2 is a diagram showing that the antibacterial peptide has no effect on eukaryotic cell growth. Jurkat cultures seeded at low density were grown in the presence of the SMRwt or the SMRmut peptide. A small but consistent aliquot was taken from each culture daily over a period of 12 days. The cells in the aliquot were counted and the cells/ml in the culture calculated to determine culture growth. The data are shown with time on the x-axis and cell number on the y-axis.

FIG. 3 is a composite of pictures showing that mortalin is a Nef SMR-specific protein. Panel A: The SMRwt peptide (lane 1) immunoprecitetated Jurkat cell proteins with molecular weights of 60, 65, 75 and 250 kDa (black circles) that were visible be Coomassie staining, and which were not pulled down in its absence (lane 2), or with the SMRmut peptide (Lane 3). Panel B; An α-martalin antibody reacted with an about 75 kDa protein in the Jurkat cell lysate (lane 1), the SMRwt peptide eluate (Lane 3), and the post-elution SMRwt peptide affinity resin (Lane 5), but failed to react with any proteins pulled down with the SMRmut peptide (Lane 4), or in the absence of either peptide (Lane 2).

FIG. 4 is a composite of diagrams showing that knockdown of mortalin results in decreased Nef secretion. Panel A: NefGFP and either anti-tubulin antibody, anti-Martalin antibody or no antibody were cotransfected into Jurkat cells by Chariot. At 48 hr post-transaction, green fluorescence protein (GFP) was assayed in the supernatant as a measure of Net-induced secretion. Panel B: NefRFP and either anti-Martalin RNAi or a negative control RNAi, or medium only were cotransfected into Jurkat cells. At 24 and 48 hr post-transfection, red fluorescence protein (RFP) was assayed in the supernatant as a measure of Nef-induced secretion.

FIG. 5 is a composite of diagrams showing that the SMRwt peptide disrupts tumor exosome release. MDA-MB-231 breast cancer cells were treated with increasing concentrations of the antagonist peptide (panel A), or negative control peptide (panel B). Extracellular AchE was analysed by Western as a marker for tumor exosome release. sM1 is a random peptide.

FIG. 6. SMRwt peptide disrupts drug-resistant growth/survival. *E. coli* (2×106) transformed with pUC18 were grown in the presence of various concentrations (x-axis) of either the antibacterial peptide (SMRwt) or negative control (SMRmut) for 6 hrs. The resultant bacteria were plated on LB plates+KAN (kanamycin; panel A), or +AMP (ampicillm; panel B). The colonies were counted (y-axis) and the data was plotted as a function of peptide dosage. The LD50 (thin dotted line) is shown for SMRwt antibacterial peptide in the presence of each bacterial resistance gene.

FIG. 7. SMRwt antibacterial peptide disrupts bacterial growth/survival. *E. coli* (2×106) transformed with pUC-4K (KAN+(panel A) or pUC18 (AMP+) (panel B) were grown in L-broth the presence of various concentrations (x-axis) of either the antagonist (SMRwt) or the negative control peptide (SMRmut) for 12 hrs. The resultant bacteria were plated on antibiotic free LB plates (pUC-4K; panel A), or pUC18; panel B). The colonies were counted (y-axis) and the data was plotted as a function of peptide dosage.

FIG. 8. Interaction between the antibacterial peptide and DnaK. *E. coli* was grown in media without antibiotics. The cells were lysed, and the resultant lysate screened by immuno-precipitation with ANTI-FLAG® M2 Affinity Gel pins either the SMRwt, SMRmut peptide, or in the absence of both peptides. Bound proteins/peptides were eluted, the eluted proteins separated by SDS-PAGE, Western blot analysis was performed using mouse monoclonal DnaK antibody (1:1000) and Thermo Scientific Immunopure® Goat Anti-Mouse IgG (H+L), Peroxidase Conjugated secondary antibody (1:2000). Lane 1, *E. coli* lysate; lane 2, no peptide eluate; lane 3, SMRwt eluate; lane 4, SMRmut eluate.

DETAILED DESCRIPTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention.

One aspect of the present invention relates to a method for treating a microbial infection, comprising: administering to a subject in need of such treatment an effective amount of an antimicrobial peptide comprising a first antimicrobial domain comprising at least one VGFPV (SEQ ID NO: 1) motif or at least one VGVSV (SEQ ID NO: 2) motif, or an effective amount of an expression vector that encodes the antimicrobial peptide and expresses the antimicrobial peptide in the subject.

Microbial Infections

As used herein, the term "Microbial infections" refers to an infection caused by bacteria, fungi and/or protozoans.

Exemplary bacteria include, but are not limited to, *Staphylococcus* species, including *S. epidermidis, S. aureus*, and methlcillin-resistant *S. aureus; Enterococcus* species, including *E. faecalis* and *E. faecium; Mycobacterium tuberculosis, Haemophilus influenzae, Pseudomonas* species, including *P. aeruginosa, P. pseudomallei* and *P. mallei; Salmonella* species, including *S. enterocolitis, S. typhimurium, S. enteritidis, S. bongori*, and *S. chloeraesuis; Shigella* species, including *S. flexneri, S. sonnei, S. dysenteriae*, and *S. boydii; Brucella* species, including *B. melitensis, B. suis, B. abortus*, and *B. pertussis; Neisseria* species, including *N. meningitidis*, and *N. gonorrhoeae; Escherichia coli*, including *enterotoxigenic E. coli* (ETEC); *Vibrio cholerae, Helicobacter pylori, Chlamydia trachomatis, Clostridium difficile, Cryptococcus neoformans, Moraxello catarrhalis, Campylobacter* species, including *C. jejuni; Corynebacterium* species, including *C. diphtheriae, C. ulcerans, C. pseudotuberculosis, C. pseudodiphtheriticum, C. urealyticum, C. hemolyticum, C. equi; Streptococcus* species, including *S. pneumoniae, S. pyogenes, S. mutans, S. agaimilae, S. equi, S. canis, S. bovis, S. equinus, S. anginosus, S. sanguis, S. salivarius, S. mitis; Listeria monocytogenes, Nocardia asteroides, Bacteroides* species, *Actinomycetes* species, *Treponema pallidum, Leptospirosa* species, *Klebsiella pneumoniae; Proteus* sp., including *Proteus vulgaris; Serratia* species. *Acinetobacter, Yersinia* species, including *Y. pestis* and *Y. pseudotuberculosis; Francisella tularensis, Enterobacter* species, *Bacteriodes* species, *Legionella* species, *Borrelia burgdorferi*, and the like.

Exemplary fungi include, but are not limited to, *Aspergillus* species. *Dermatophytes, Blastomyces derinatitidis, Candida* species, including *C. albicans* and *C. krusei; Malassezia furfur, Exophiala werneckii, Piedraia hortai, Trichosporon beigelii, Pseudallescheria boydii, Madurella grisea, Histoplasma capsulatum, Sporothrix schenckii, Histoplasma capsulatum, Tinea* species, including *T. versicolor, T. pedis T. ungulum, T. cruris, T. capitus, T. corporis, T. barbae; Trichophyton* species, including *T. rubrum, T. interdigitale, T. tonsurans, T. violaceum, T. yaoundei, T. schoenleinii, T. megninii, T. soudamense, T. equinum, T. erinacei*, and *T. verruscostam; Microsporum* species, including *M. audouini, M. ferrugineum, M. canis, M. nanum, M. distortum, M. gypseum, M. fulvum*, and the like.

Exemplary protozoans include, but are not limited to *Cryptosporidium, Isospora belli, Toxoplasma gondii, Trichomonas vaginalis*, and *Cyclospora* species.

The Antimicrobial Peptide

The antimicrobial peptide can be of various length. In certain embodiments, the antimicrobial peptide has a length of 10-200 amino acids, 10100 amino acids or 10-50 amino acids and comprises at least one VGFPV (SEQ ID NO: 1) motif. In other embodiments, the antimicrobial peptide comprises at least two VGFPV (SEQ ID NO: 1) motifs. In certain other embodiments, the antimicrobial peptide comprises 2, 3, 4, 5, 6, 7, 8 or more VGFPV (SEQ ID NO: 1) motifs. In other embodiments, the antimicrobial, peptide comprises at least one VGFPV (SEQ ID NO: 1) motif at the N-terminal. In other embodiments, the antimicrobial peptide comprises at least one VGFPV (SEQ ID NO: 1) motif at the C-terminal. In other embodiments, the antimicrobial peptide comprises the amino acid sequence of VGFPVAAVGFPV (SEQ ID NO: 3). In other embodiments, the antimicrobial peptide comprises at lease one VGVSV (SEQ ID NO: 2) motif. In other embodiments, the antimicrobial peptide comprises at least two VGVSV (SEQ ID NO: 2) motifs. In other embodiments, the antimicrobial peptide comprises at least one VGFPV (SEQ ID NO: 1) motif and at least one VGVSV (SEQ ID NO: 2) motif. In yet other embodiments, the antimicrobial peptide comprises the amino acid sequence of VGVSVAAYGVSV (SEQ ID NO: 4).

In other embodiments, the antimicrobial peptide of the present invention further comprises a second antimicrobial domain that comprises a known AMP sequence. The known AMP sequence enhances the antimicrobial activity of the antimicrobial peptide of the present invention and/or facilitate the uptake of the antimicrobial peptide by the microorganism. Examples of known AMPs include, but are not limited to, andropin, apidaecin, bacteriocin leucocin A, bactenecin, bactenecin-7, buforin II, cathelicidin LL-37, clavanin A, cecropin, cecropin A-magainin 2 hybrid peptide, dermcidin-1L, cyclic dodecapeptide, β-defensin I, α-defensin (HNP-1), E3-APO, gaegurin, histatin, histatin-5, indolicidin, magainin 2, melittin B, nisin A, novispirin G10, pyrrhocoricin, protegrin, protegrin PG-1, ranalexin, tachyplesin-1, and tachyplesin-1 analog.

In other embodiments, the antimicrobial peptide of the present invention further comprises a cell penetrating peptide (CPP) domain. A CPP domain enhances the uptake of the antimicrobial peptide of the present invention by an eukaryotic cell. Exemplary CPP domains for use in the present invention include, but are not limited to, HIV $TAT_{49-57}$ peptide, HIV $TAT_{48-60}$ peptide, low molecular weight protamine (LMWP) peptide; Chariot™, also known as Pep-1 (Morris et al., *Nat. Biotechnol.*, 19:1173-1176, 2001); Antp$_{43-58}$ peptide, MPG (HIV Gp41-SV40 NLS), SAP, MPG R9, MAP, K-FGF, Penetratin, Buforin II, Transport, Ku70, Prion, pVEC, Pep-1-K, Pep-7, HN-1, TP10, and CP26 (See e.g., Joliot et al. *Nature Cell Biol.*, 6(3):189-196, 2004 and Heitz et al., *Br. J. Pharmacol.*, 157:195-206, 2009).

In other embodiments, the antimicrobial peptide of the present invention further comprises a targeting domain. The targeting domain allows the antimicrobial peptide of the present invention to be targeted to one or more desired microorganisms of interest. In a specific embodiment, the targeting domain comprises an antibody-derived epitope binding domain or other cellular ligand capable of binding to a surface molecule of the microorganism of interest.

Exemplary epitope binding domains include, but not limited to a member of the group consisting of: IgG, antibody variable region; isolated CDR region; single chain Fv molecule (scFv) comprising VH and VL domain linked by a peptide linker allowing for association between the two domains to form an antigen binding site; bispecific scFv dimer; minibody comprising a scFv joined to a CH3 domain, single chain diabody fragment, dAb fragment, which consists of a VH or a VL domain; Fab fragment consisting of VL, VH, CL and CH1 domains; Fab' fragment, which differs from a Fab fragment, by the addition of a few residues at the carboxyl terminus of the heavy chain CH1 domain, including one or more cysteines from the antibody binge region; Fab'-SH fragment, which is a Fab' fragment in which the cysteine residue(s) of the constant domains bear a free thiol group; F(ab')2, bivalent fragment comprising two linked Fab fragments; Fd fragment consisting of VH and CH1 domains; derivatives thereof, and any other antibody fragment(s) retaining antigen-binding function, Fv, scFv, or diabody molecules may be stabilized by the incorporation of disulphide bridges linking the VH and VL domains. Preferably, the epitope binding domain is selected to target and specifically bind to an antigen expressed on the surface of a particular target microorganism of interest.

In other embodiments, the targeting domain comprises a cell surface receptor-binding ligand or cell-binding peptide isolated from a phage display library, for example. Phage display libraries engineered for binding cell surface molecules or receptors are well known to those of skill in the art.

The antimicrobial peptide of the present invention, may contain one or more targeting domains. When using a plurality, the targeting domains may be the same or different. In addition the one or more targeting domain(s) may be further linked to an Fc region. The Fc region can facilitate recruitment of Fc receptor-bearing natural killer cells, macrophages, neutrophils, and mast cells, which can stimulate phagocytic or cytotoxic cells to destroy microbes or infected cells by antibody-mediated phagocytosis or antibody-dependent cell-mediated cytotoxicity. Further, when using antibody-derived targeting agents, any or all of the targeting domains therein and/or Fc regions maybe "humanized" using methodologies well known to those of skill in the art.

In certain embodiments, the antimicrobial peptide of the present invention further comprises one or more spacers or linkers that link different domains, such as the first and the second antimicrobial domains, the CPP domain and the targeting domain, within the antimicrobial peptide. The spacer or linker is designed to facilitate the independent folding of each domain relative to one another and ensure that the individual domains in the peptide do not interfere with one another or with the SMR peptide. The spacer may include any amino acid or mixtures thereof. In one embodiment, the spacer comprises between 1 to 50 amino acids, preferably 3 to 10 amino acids in length.

Preferably, the spacer will be designed to increase the flexibility of the protein and facilitate adoption of an extended conformation. For example, the spacer may have a high glycine content to force the spacer to adopt a loop conformation. Glycine is favored for use in spacers because the absence of a β-carbon permits the polypeptide backbone to access dihedral angles that are energetically forbidden for other amino acids. In addition, spacers comprising glycine and/or serine have a high freedom degree for linking of two peptides, i.e., they enable the fused proteins to fold and produce functional proteins. Preferably, the spacer comprises hydrophilic residues enhancing stability and folding of the fusion protein, and will include other residues other than glycine, such as, for example, alanine or serine. Preferred peptide spacers are comprised of the amino acids proline, lysine, glycine, alanine, and/or serine, and combinations thereof. In one embodiment, the linker is a glycine rich linker. In a particular embodiment, the spacer having the formula [(Gly)$_n$-Ser/Ala]$_m$ where n is from 1 to 4, inclusive, and m is from 1 to 4, inclusive.

The antimicrobial peptide of the present invention may be chemically modified using one or more methods including, but not limited to, amidation, acetylation (including N-terminal acetylation), carboxylation, glycosylation, methyiation (e.g., substitution of α-hydrogens with methyl groups), carbonylatlon, phosphorylation, PEGylation, dimerization, addition of interchain and/or intrachain disulfide bonds, addition of trans olefin, derivatization by known protecting/blocking groups, circularization, substitution with D amino acids, linkage to an antibody molecules or other cellular ligands, etc.

Additional modifications include, for example, point mutations, insertions, deletion, truncation, and backbone substitutions, such as NH to NCH$_3$. In addition, the peptide may be modified by the insertion of one or more D amino acids. Further, proline analogs in which the ring sixe of the proline residue is changed from 5 members to 4, 6, or 7 members can be employed. Cyclic groups can be saturated or unsaturated, and if unsaturated, can be aromatic or non-aromatic In one embodiment, the antimicrobial peptide comprises a modified C-terminus and/or a modified N-terminus. For example, the N-terminus can be acetylated (Ac) and/or the C-terminus can be amidated (NH$_2$). Where the C-terminus is amidated, the carboxylic acid of the amino acid is converted to an amide, i.e., NH$_2$—CH$_2$—C(O)—NH$_2$.

The antimicrobial peptide may further contain one or more covalently attached functional groups, preferably attached to either or both of the N and C termini of the polypeptide. These covalently attached groups can include stabilizers, couplers, ligands, enzymatic substrates and/or combinations thereof. Preferred groups include acyl groups on the N terminus and cysteamine (cya) coupling groups on the C terminal end. To the latter may be conveniently attached other chemical moieties, e.g., dyes, ligands, proteins, enzymes, enzymatic substrates, etc. Alternatives to cya are also known to those of skill in the art. For stabilizing and/or blocking, e.g., cya may be replaced with an alky group such as methyl or ethyl, which are known to be conveniently positioned onto a —COOH group.

N-terminal modifications additionally include, but are not limited to, methylating (i.e., —NHCH3 or —NH(CH3)2), adding a 1-amino-cyclohexane-carboxylic acid moiety (Chex); and adding a carbobenzoyl group, or blocking the amino terminus with any blocking group containing a carboxylase functionality defined by RCOO—, where R is selected from the group consisting of naphthyl, acridinyl, steroidyl, and similar groups.

A derivitizing group, including, but not limited to, a sulfhydryl-containing group or moiety may be positioned at the C-terminus of the AMFP, even when it is not coupled to another chemical moiety. In one embodiment, the C-terminal end may be modified with a cysteamide group (—NH—CH2-CH2-SH), which can allow further coupling to drugs. A cysteamide group is compatible with the peptide synthesis using the Fmoc strategy and leads to a C-terminal protected peptide. Alternatively, the peptide can include a C-terminal cysteine residue containing a sulfhydryl (—SH) group that can be optionally utilized for conjugation to other moieties. In another embodiment, the C-terminal end includes a 2,4-diamino-butyric acid (DAB) moiety. C-terminal modifications may further include replacing the free acid with a carboxamide group or forming a cyclic lactam at the carboxy terminus to introduce structural constraints.

Naturally occurring side chains of the 20 genetically encoded amino acids (or D amino acids) may be replaced with other side chains with similar properties, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic.

Such substitutions can include but are not necessarily limited to: (1) non-standard positively charged amino acids, like: ornithine; N-(4-aminobutyl)-glycine having a lysine side chain attached to the "N-terminus" and aminoptopyl or aminoethyl groups attached to the amino group of glycine; (2) Non-naturally occurring amino acids with no net charge and sidechains similar to arginine, such as citrulline, with or without methylene groups; (3) non-standard non-naturally occurring amino acids with OH (e.g., serine), such as, homoserine, hydroxyproline, hydroxyvaline; and penicillamin; (4) proline derivatives, such as, D-Pro, including 3,4-dehydroproline, pyroglutamine, proline with fluorine substitutions on the ring, 1,3-thiazolidine-4-carboxylic acid; (5) Histidine derivative, such as beta-(2-thienyl)-alanine; or (6) alkyl derivatives, such as 2-aminobutyric acid, norvaline, norleucine, homoleucine, and alpha-aminoisobutyric acid.

In another embodiment, the C-terminal carboxyl group or a C-terminal ester may be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH2Cl2), dimethyl formamide (DMF) mixtures. The cyclic peptide is then formed by internal displacement of the activated ester with the N-terminal amine, internal cyclization as opposed to polymerization can be enhanced by use of very dilute solutions. Such methods are well known in the art.

In other embodiments, the antimicrobial peptide of the present invention is cyclized or includes a desamino or descarboxy residue at the peptide terminal so that there are no terminal amino or carboxyl groups. This can decrease susceptibility to proteases and/or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and pharmaceutically acceptable salts thereof. The antimicrobial peptide may be cyclized by adding an N and/or C terminal cysteine and cyclizing the peptide through disulfide linkages or other side chain interactions.

In some embodiments, the antimicrobial peptides of the present invention are synthesized using traditional liquid- or solid-phase synthesis. Fmoc and t-Boc solid phase peptide synthesis (SPPS) can be employed to grow the peptides from carboxy to amino-terminus. In certain embodiments, the last "amino acid" added to the reaction is PEGylated. This last amino acid is often referred to as a carboxyl-PEG-amine, carboxyl-PEO-amine, or amine-PEG-acid, whereby the amine is blocked to protect against reaction and the acid is free to react with the amine group from the previously added amino acid in the reaction. PEG (polyethylene glycol) and PEO (polyethylene oxide) are polymers composed of repeating sub-units of ethylene glycol and ethylene oxide monomers. In one embodiment, the PEG moiety is 5 to 30 kDa in size. In another embodiment, the PEG moiety is 10 to 20 kDa in size.

In addition to using PEGylated end amino acid during synthesis, the antimicrobial peptide of the present invention may be PEGylated by PEGylation. PEGylation is the process of covalent attachment of polyethylene glycol polymer chains to another molecule, normally a drug or therapeutic protein. PEGylation can be achieved by incubation of a reactive derivative of PEG with the antimicrobial peptide. The covalent attachment of PEG to a antimicrobial peptide can "mask" the antimicrobial peptide from the host's immune system (reduced immunogenicity and antigenicity), increase the hydrodynamic size (size in solution) of the antimicrobial peptide which prolongs its circulatory time by reducing renal clearance. PEGylation can also provide water solubility to hydrophobic proteins.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehyde functional polymers.

In certain embodiments, the PEG derivatives are produced by reacting the PEG polymer with a group that is reactive with hydroxyl groups, typically anhydrides, acid chlorides, chloroformates and carbonates. In other embodiments, more efficient functional groups such as aldehyde, esters, amides, etc. are made available for protein conjugation.

In certain embodiments, heterobifunctional PEGs are used for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters. In other embodiments, the pegylation agents contain branched, Y shaped or comb shaped polymers that show reduced viscosity and lack of organ accumulation. Any other enhancers of pharmacokinetics (PK) and/or pharmacodynamics (PD) may also be used In other embodiments, the antimicrobial peptides of the present application are linked to transferrin or siderophores, such as pesticin, that bind to receptors on bacteria surface.

Treatment or Prevention of Microbial Infections

An antimicrobial agent, such as the antimicrobial peptide of the present application, has the capacity to kill, disrupt the reproduction of, inhibit the growth of, or reduce the drug-resistance of a microorganism.

In certain embodiments, the antimicrobial peptide is used for the treatment or prevention of bacterial infection. Exemplary bacteria for treatment include, but are not limited to, *Staphylococcus* species, including *S. epidermidis*, *S. aureus*, and methicillin-resistant *S. aureus*; *Enterococcus* species, including *E. faecalis* and *E. faecium*; *Mycobacterium tuberculosis*, *Haemophilus influenzae*, *Pseudomonas* species, including *P. aeruginosa*, *P. pseudomallei*, and *P. mallei*; *Salmonella* species, including *S. enterocolitis*, *S. typhimurium*, *S. enteritidis*, *S. bongori*, and *S. choleraesuis*; *Shigella* species, including *S. flexneri*, *S. sonnei*, *S. dysenteriae*, and *S. boydii*; *Brucella* species, including *B. melitensis*, *B. suis*, *B. abortus*; and *B. pertussis*; *Neisseria* species, including *N. meningitidis* and *N. gonorrhoeae*; *Escherichia coli*, including enterotoxigenic *E. coli* (ETBC); *Vibrio cholerae*, *Helicobacter pylori*, *Chlamydia trachomatis*, *Clostridium difficile*, *Cryptococcus neoformans*, *Moraxella catarrhalis*, *Campylobacter* species, including *C. jejuni*; *Corynebacterium* species, including *C. diphtheriae*, *C. ulcerans*, *C. pseudotuberculosis*, *C. pseudodiphtheriticum*, *C. urealyticum*, *C. hemolyticum*, *C. equi*; *Streptococcus* species, including *S. pneumoniae*, *S. pyogenes*, *S. mutans*, *S. agalactiae*, *S. egui*, *S. canis*, *S. bovis*, *S. equinus*, *S. anginosus*, *S. sanguis*, *S. salivarius*, *S. mitis*; *Listeria monocytognes*, *Nocardia asteroides*, *Bacteroides* species, *Actinomycetes* species, *Treponema pallidum*, *Leptospirosa* species, *Klebsiella pneumoniae*; *Proteus* sp., including *Proteus vulgaris*; *Serratta* species, *Acinetobacter*, *Yersinia* species, including *Y. pestis* and *Y. pseudotuberculosis*; *Francisella tularensis*, *Enterobacter* species, *Bacteriodes* species, *Legionella* species, *Borrelia burgdorferi*, and the like.

In other embodiment, the antimicrobial peptide is used for the treatment or prevention of fungi infections. Exemplary fungi for treatment include, but are not limited to, *Aspergillus* species, *Dermatophytes*, *Blastomyces derinatitidis*, *Candida* species, including *C. albicans* and *C. krusei*; *Malassezia furfur*, *Exophiala werneckii*, *Piedraia hortai*, *Trichosporon beigelii*, *Pseudallescheria boydii*, *Madurella grisea*, *Histoplasma capsulaium*, *Sporothrix schenckii*, *Histoplasma capsulaium*, *Tinea* species, including *T. versicolor*, *T. pedis* *T. unguium*, *T. cruris*, *T. capitus*, *T. corporis*, *T. barbae*; *Trichophyton* species, including *T. rubrum*, *T. interdigitale*, *T. tonsurans*, *T. violaceum*, *T. yaoundei*, *T. schoenleinii*, *T. megninii*, *T. soudanese*, *T. equinum*, *T. erinacei*, and *T. verrucosum*; *Microsporum* species, including *M. audouini*, *M. ferrugineum*, *M. canis*, *M. nanum*, *M. distortum*, *M. gypseum*, *M. fulvum*, and the like.

In other embodiments, the antimicrobial, peptide is used for the treatment or prevention of protozoan infections, such as infections by *Cryptosporidium*, *Isospora belli*, *Toxoplasma gondii*, *Trichomonas vaginalis*, and *Cyclospora* species.

In other embodiments, the antimicrobial peptide may be useful for treating or preventing a variety of conditions including, for example, an infections of the skin, infectious of the urogenital tract, infections of the digestive system (e.g., the gut), infectious of the lung, and/or infections of the sinus. For example, the antimicrobial compositions may be useful for the treatment of a condition, such as, for example, rosacea, atopic dermatitis (e.g., eczema), a *Candida* infection (e.g., vaginal diaper, intertrigo, balanitis, oral thrush). *Tinea versicolor*, Dermatophytosis (e.g., *Tinea pedis* (athlete's foot)), *Tinea unguium*, Onychomycosis (e.g., toe nail fungus). *Tinea cruris*, *Tinea capitus*, *Tinea corporis*, *Tinea barbae*, seborrheic dermatitis, antibiotic-resistant skin infections, impetigo, ecthyma, erythrasma, burn wounds (e.g., reduction of infections, improved healing), diabetic foot/leg ulcers (e.g., reduction of infections, improved healing), prevention of central catheter-related blood stream infections, oral mucositis, warts (e.g., common, flat, plantar, genital), and molluseum contagiosum. In some embodiments, the condition is acne, often acne vulgaris and sometimes acne conglobate.

Route and Dose of Antimicrobial Peptide Administration

The antimicrobial peptide of the present invention may be administered orally, intrathecally, intra-arterially, intravenously, intradermally, subcutaneously, transdermally (topically) or transmucosally. An antimicrobial composition may be administered by any route, including oral, rectal, pulmonary, sublingual, and parenteral administration. Parenteral administration includes, for example, intraperitoneal, intravenous, intramuscular, intraarterial, intravesical (e.g., to the bladder), intradermal, transdermal, topical, or subcutaneous administration.

As a general proposition, the therapeutically effective amount of the antimicrobial peptide administered will be in the range of about 1 ng/kg body weight/day to about 100 mg/kg body weight/day whether by one or more administrations. In a particular embodiment, the range of antimicrobial peptide administered is from about 1 ng/kg body weight/day to about 1 µg/kg body weight/day, 1 ng/kg body weight/day to about 100 ng/kg body weight/day, 1 ng/kg body weight/day to about 10 ng/kg body weight/day, 10 ng/kg body weight/day to about 1 µg/kg body weight/day, 10 ng/kg body weight/day to about 100 ng/kg body weight/day, 100 ng/kg body weight/day to about 1 µg/kg body weight/day, 100 ng/kg body weight/day to about 10 µg/kg body weight/day, 1 µg/kg body weight/day to about 10 µg/kg body weight/day, 1 µg/kg body weight/day to about 100 µg/kg body weight/day, 10 µg/kg body weight/day to about 100 µg/kg body weight/day, 10 µg/kg body weight/day to about 1 mg/kg body weight/day, 100 µg/kg body weight/day to about 10 mg/kg body weight/day, 1 mg/kg body weight/day to about 100 mg/kg body weight/day and 10 mg/kg body weight/day to about 100 mg/kg body weight/day.

In other embodiments, the antimicrobial peptide is administered at a dosage range of 1 ng-10 ng per injection, 10 ng-100 ng per injection, 100 ng-1 µg per injection, 1 µg-10 µg per injection, 10 µg-100 µg per injection, 100 µg-1 mg per injection, 1 mg-10 mg per injection, 10 mg-100 mg per injection, and 100 mg-1000 mg per injection. The antimicrobial peptide may be injected daily, or every 2, 3, 4, 5, 6 and 7 days.

In other embodiments, the dose range of the antimicrobial peptide administered is from about 1 ng/kg to about 100 mg/kg. In still another particular embodiment, the range of antibody administered is from about 1 ng/kg to about 10 ng/kg, about 10 ng/kg to about 100 ng/kg, about 100 ng/kg to about 1 µg/kg, about 1 µg/kg to about 10 µg/kg, about 10 µg/kg to about 100 µg/kg, about 100 µg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the amount of antimicrobial peptide administered is, or is about 0.0006, 0.001, 0.003, 0.006, 0.01, 0.03, 0.06, 0.1, 0.3, 0.6, 1, 3, 6, 10, 30, 60, 100, 300, 600 and 1000 mg/day.

The specific dose of antimicrobial peptide is determined by the particular circumstances of the individual pattern including the size, weight, age and sex of the patient, the nature and stage of the disease, the aggressiveness of the disease, and the route of administration of the antimicrobial composition.

In certain embodiments, the antimicrobial peptide may be administered at least once per day, typically once, twice, three times or four times per day with the doses given at equal intervals throughout the day and night in order to maintain a constant presence of the drug in order to provide sufficient antibacterial activity. However, a skilled artisan will appreciate that a treatment schedule can be optimized for any given patient, and that administration of compound may occur less frequently than once per day.

In other embodiments, the antimicrobial peptide of the present invention is prescribed to be taken in combination with other antimicrobial agents. Examples of other antimicrobial agents include, but are not limited to, antibiotics, other antimicrobial peptides, bacterial biofilm-degrading enzymes and in vivo expression vectors that encode the antimicrobial peptide of the present invention. When used in such combinations, the antimicrobial peptide of the present invention and other antimicrobial agents may be administered simultaneously, by the same or different routes, or at different times during treatment.

The treatment may be carried out for as long a period as necessary, i.e., until the infection is cleared or no longer a threat to the host. Typically it is contemplated that treatment would be continued indefinitely while the disease state persists, although discontinuation might be indicated if the antimicrobial compositions no longer produce a beneficial effect. The treating physician will know how to increase, decrease, or interrupt treatment based on patient response.

Production of the Antimicrobial Peptide

The antimicrobial peptide of the present invention can be chemically synthesized or produced from cells transformed with polynucleotide expression vectors encoding the antibacterial peptide using recombinant DNA technologies well known to those skilled in the art. Polynucleotide expression vectors can be designed to facilitate preparative expression levels in many different cell hosts, including bacteria, yeast, insect cells, and mammalian cells.

In some microorganisms, such as wild type E. coli, the periplasm constitutes an oxidizing environment, whereas the cytoplasm is a reducing environment. Accordingly, expression in the E. coli periplasm may enable the production of peptides containing interchain or intrachain disulfide bonds that might be otherwise reduced in cytoplasm, where it may be toxic to the cell. Some prokaryotic organisms have endogenous, intracellular oxidizing environments and can normally accommodate formation of protein disulfide bonds inside the cell. Accordingly, the fusion protein may be periplasmically expressed using an operably linked periplasmic signal sequence at the 5' end of the corresponding nucleic acid expression construct.

The antimicrobial peptide encoded in the expression vector may further include a cleavage recognition site for proteolytic cleavage of one or more peptide domains from one another. The cleavage recognition sequence can be cleaved by a suitable protease, such as Kex2p or furin, at one or more defined residues.

Where the cleavage recognition site is positioned adjacent to an antimicrobial domain, proteolytic cleavage in a transduced cell can liberate one or more antimicrobial domains from one another so that the antimicrobial agents can function independently of one another according to their designated microbial cell surface target or microbial intracellular target.

For example, when positioned in or adjacent to an antimicrobial peptide spacer region, the peptide can be directly cleaved when introduced into a microbial cell bearing the corresponding protease. In one embodiment, the proteolytic recognition site is a Kex2p-sensitive proteolytic cleavage site. In another embodiment, the proteolytic recognition site is the furin proteolytic cleavage site, which is sensitive to cleavage by the enzyme, furin.

An expression construct can further include an N-terminal signal peptide region to facilitate entry of the encoded antimicrobial peptide into the secretory pathway following gene transfer into eukaryotic cells near a site of infection.

In vivo Expression Vectors Encoding the Antimicrobial Peptide

In certain embodiments, an expression vector encoding the antimicrobial peptide of the present invention is directly administered to a patient to express the antimicrobial peptide in vivo. Suitable non-viral expression vectors include, but are not limited to, plasmid expression vector or a bacteriophage vectors. Suitable viral vectors include, but are not limited to, retroviral vectors, lentiviral vectors, adenoviral vectors, adeno-associated viral (AAV) vectors, herpes viral vectors, and alphavirus vectors. The viral vector can also be an astrovirus, coronavirus, orthomyxovirus, papovavirus, paramyxovirus, parvovirus, picornavirus, poxvirus, togavirus viral vector.

The term "in vivo expression vector" refers to a non-viral or viral vector that comprises a polynucleotide encoding the antimicrobial peptide of the present invention in a form suitable for expression of the polynucleotide in a host cell. The expression vectors include one or more regulatory sequences, selected on the basis of the host cells to be used for expression, and operably linked to the polynucleotide sequence to be expressed. It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, such as the antimicrobial peptide of the present application.

As used herein, the term "control sequences" or "regulatory sequences" refers to DNA sequences necessary for the expression of an operably linked coding sequence in a particular host organism. The term "control/regulatory sequence" is intended to include promoters, enhancers and other expression control elements (e.g., polyadenylation signals). Control/regulatory sequences include those which direct constitutive expression of a nucleotide sequence in many types of host cells and those which direct expression of the nucleotide sequence only in certain host cells ( e.g., tissue-specific regulatory sequences). An expression vector may be designed to facilitate expression of the antimicrobial peptide-encoding polynucleotide in one or more cell types. Tissue-specific regulatory elements may be used to restrict expression to a particular cell type.

A nucleic acid sequence is "operably linked" to another nucleic acid sequence when the former is placed into a functional relationship with the latter. For example, a DNA for a presequence or secretory leader peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

The delivery of antimicrobial peptide-encoding expression vectors can be achieved by infection (for viral vectors), transfection (for non-viral vectors) and other methods well known to one skilled in the art. Examples of other delivery methods and media include, polycationic condensed DNA linked or unlinked to killed viruses, ligand linked DNA, liposomes, eukaryotic cell delivery vehicles cells, deposition of photopolymerized hydrogel materials, handheld gene transfer particle gun, ionizing radiation, nucleic charge neutralization or fusion with cell membranes. Particle mediated gene transfer may also be employed.

Plasmid DNA expression vectors can be utilized for non-vital gene transfer, either by direct injection of naked DNA or by encapsulating the antimicrobial peptide-encoding polynucleotides in liposomes, microparticles, microcapsules, virus-like particles, or erythrocyte ghosts. Such compositions can be further linked by chemical conjugation to, for example, microbial translocation domains and/or targeting domains to facilitate targeted delivery and/or entry of nucleic acids into the nucleus of desired cells to promote gene expression. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin. Naked DNA may also be employed. Uptake efficiency of naked DNA may be improved using biodegradable latex beads. Such delivery may be improved further by treating the beads to increase hydrophobicity and thereby facilitate disruption of the endosome and release of the DNA into the cytoplasm.

Bacteriophage Vectors

In certain embodiments, the expression vectors comprises a bacteriophage displaying the antimicrobial peptide on its surface, or expressed from a bacteriophage following entry into a bacterium, or both. The bacteriophage can be specific for groups of bacteria or single strains. Bacteriophages can provide high titer incoculums and amplified spread, wherein a single particle can produce between about 10-100 particles per phage. Displaying the fusion protein on the phage surface can render the particle bactericidal, irrespective of whether the transduced cell is capable of supporting bacteriophage replication and spread.

In certain embodiments, the antibacterial peptide of the present invention is recombinantly expressed from a bacteriophage in bacterial target cells permissive to bacteriophage infection. Where the cell is a microbial cell permissive for a bacteriophage genetically engineered to express the antibacterial peptide, the cell can be killed directly and program the synthesis of additional bacteriophages for amplifying the bacterial cell killing effects.

In other embodiments, the antibacterial peptide is displayed on the bacteriophage surface as part of phage tail fiber or coat protein using phage display technologies well known to those of skill in the art. The antibacterial peptide or bacteriophage may additionally include a targeting domain to facilitate targeted killing of a specified bacterial Gram-designation, genus, species, or strain. By way of example, a DNA encoding an antibacterial peptide comprising an SMR domain and one or more CPP domains, targeting domains, and/or other antimicrobial domains may be displayed onto a major or minor coat protein, of a filamentous bacteriophage, for example in Proteins I through VIII of phages SAP-2, M13, or T7. In addition, the bacteriophage may be modified to display a fusion protein comprising a Protein A portion or other suitable Fc- or IgG-binding region for attachment to targeting domains, including anti-microbial IgG antibodies or other antibody-based targeting agents described herein in accordance with methodologies previously described by Yacoby et al. (Yacoby et al., Antimicrob. Agents Chemother., 50(6):2087-2097, 2006).

Where the microbial cell is non-permissive for a bacteriophage replication, the bacteriophage can nonetheless infect and kill the cell, provided that the bacteriophage displays an antimicrobial domain and/or cell penetrating peptide domain appropriate for binding to and killing of a suitable microbial target cell.

Alternatively, antimicrobial peptide and antibiotics can be chemically conjugated onto the surface of the phage particles using chemical conjugation methodologies capable of displaying between 3,000-40,000 drug (or antibiotic) molecules per phage (see, e.g., Antimicrob. Agents Chemother., 51(6):2156-22163, 2007, and U.S. Pat. Appl. No. 2008/0057038 to Yacoby et al.).

In another embodiment, the antimicrobial peptide of the present invention may be displayed on a phage tail fiber or coat protein using the sortase enzyme in combination with the appropriate substrates for sortase-mediated peptide ligation (see e.g., Proft, Biotechnol. Lett. 32(1):1-10 and U.S. Pat. Appl. Publ. No. 2011/0046008 to Love et al.).

Any bacteriophage may be used in the practice of the present invention. In one embodiment, the bacteriophage is a lytic bacteriophage. In another embodiment, the bacteriophage is lysis-deficient. In some cases, use of lysis-deficient bacteriophages may reduce in vivo toxicity by reducing endotoxin and inflammatory mediator release. Exemplary bacteriophages for use with the antibacterial fusion proteins of the present invention include, but are not limited to, filamentous bacteriophages, *Escherichia coli* bacteriophages; staphylococcal bacteriophages, including bacteriophage 456, P9042, a lytic phage, and P954, a lysogenic phage; bacteriophages that infect pseudomonal and enterococcal species, as disclosed in e.g., US Pat. Appl. Publ. No. 2011/0020290 and 2006/0140911; phage lambda, phage f1, p1 phage, phage Mu, fd, WT phage, M13, ΦX174, Φ6, Φ20, Φ29, ΦGH4, ΦDGH4, ΦDGH6, ΦDGH13, ΦDGH14, R17, T12, T7, T4, T2, A511, L5, P58, K5, K1, PM2, P22, K1-5, ENB6, IRA, SP6, twort phage, RZh, H4489a, A511::luxAB, and phAE40.

Pharmaceutical Compositions

The present invention further provides a pharmaceutical composition comprising (1) an antimicrobial peptide of the present invention, an in vivo expression vector encoding the antimicrobial peptide of the present invention, or both, and (2) a pharmaceutically acceptable carrier. In certain embodiments, the pharmaceutical composition further comprises one or more antimicrobial agents, such as other antimicrobial peptides, antibiotics and bacterial biofilm-degrading enzymes.

In certain embodiments, the antimicrobial agents comprise bacterial biofilm-degrading enzymes such as alginate lyase. In other embodiments, the antimicrobial agents comprise an antibiotics. In other embodiments, the antimicrobial agents comprise another antimicrobial peptide.

As used herein the language "pharmaceutically acceptable carrier" is intended to include any and all solvents, solubilizers, fillers, stabilizers, binders, absorbents, bases, buffering agents, lubricants, controlled release, vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. See e.g., A. H. Kibbe Handbook of Pharmaceutical Excipients, 3rd ed. Pharmaceutical Press, London, UK (2000). Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the invention is formulated to be compatible with its intended route of administration. Examples of routes of administration include parenteral, e.g., intrathecal, intra-arterial, intravenous, intradermal, subcutaneous, oral, transdermal (topical) and transmucosal administration.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose, pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene, glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an antimicrobial peptide) in the required amount in an appropriate solvent with one or a combination of ingredients enumerated above, as required, followed by filtered sterilization. Generally, dispersions are prepared by incorporating file active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and poly lactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers.

It is especially advantageous to formulate oral or parenteral compositions in dosage unit form for ease of administration and uniformity of dosage. Suitable unit dosage forms include, but are not limited to powders, tablets, pills, capsules, lozenges, suppositories, patches, nasal sprays, injectibles, implantable sustained-release formulations, lipid complexes, etc.

Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of the antimicrobial peptide of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should betaken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilised. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The present application is further illustrated by the following examples that should not be construed as limiting. The contents of all references, patents, and published patent applications cited throughout this application, as well as the Figures and Tables, are incorporated herein by reference.

EXAMPLE 1

The HIV-1 NEFSMRWT Peptide Disrupts Secretion Activity of Mortalin (DNAK Homologue)

Drug resistance caused: 1) production of enzymes that inactive or destroy the antibacterial drug; 2) modification of the drug's target site; 3) expression efflux systems that pump out the drug before it can reach its intracellular target; or 4) the production of alternative metabolic pathway that bypasses the action of the drug. Resistance genes coding for proteins that perform these functions maybe exchanged within and between bacterial species. Horizontal transfer of resistance genes occurs through transformation, transduction, or conjugation. Resistance genes can be found on plasmids, transposons and integrons, unique genetic elements able to capture, integrate and express gene cassettes encoding resistance. Cell to cell transfer of resistance genes is often facilitated by a multi-component device known as a type IV secretion system, which acts to transport antibiotic resistance genes from within one cell, through its membrane and into a neighboring cell.

Translocation of the drug-resistant gene product crosses the inner membrane, requires chaperones for transit and folding of those proteins. The chaperone protein DnaK has been shown to be a central factor in a multiprotein bacterial chaperone system that includes a variety of co-chaperone proteins such as DnaJ and GrpE. This general chaperone system is in concert with either the SecB chaperone using the Sec secretion machinery, or the second, Twin-arginine Translocation (Tat) secretion pathway. DnaK is also involved in the replication of the bacterial chromosome, and plasmids. Bacteria with mutations in the DnaK/DnaJ molecules have been found to have lower growth rates, greater susceptibility to environmental stress, reduced viability in cellular environments, reduced ability to establish infectious in vivo, and they are more susceptible to antibiotics compared to the wild-type strains. Thus, molecules targeting DnaK could disrupt bacterial growth, viability, and antibiotic drug resistance and constitute a new class of antibacterial therapeutic.

Figure 1:
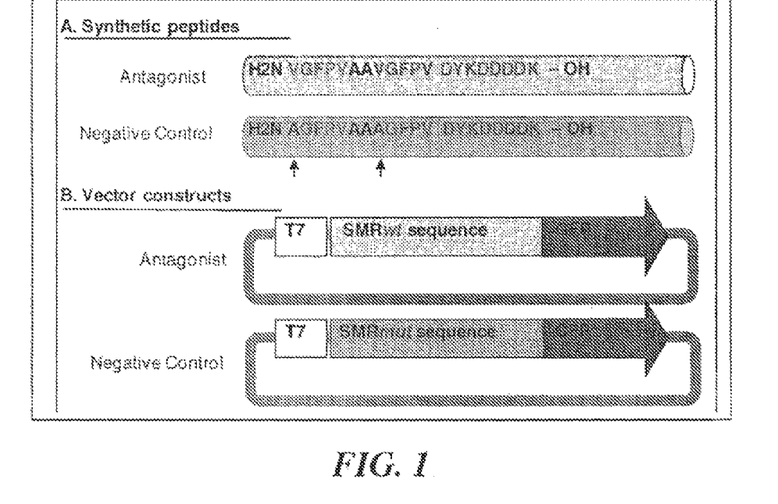
Figure 2:
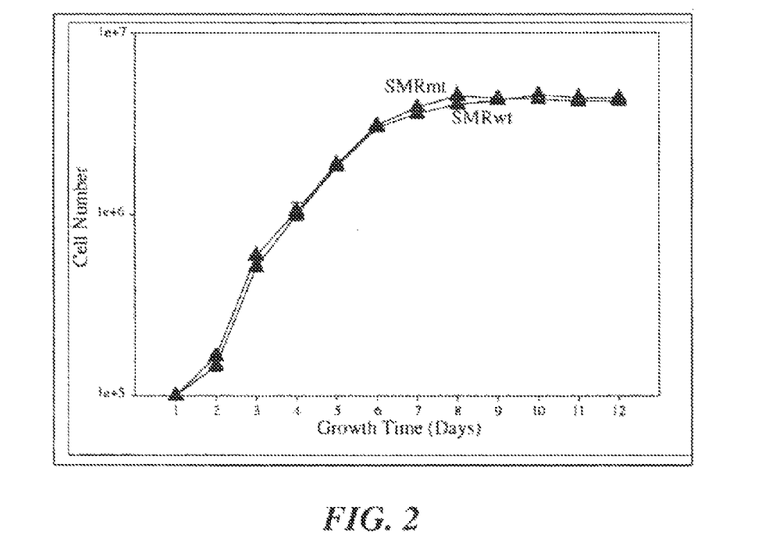
Figure 3:
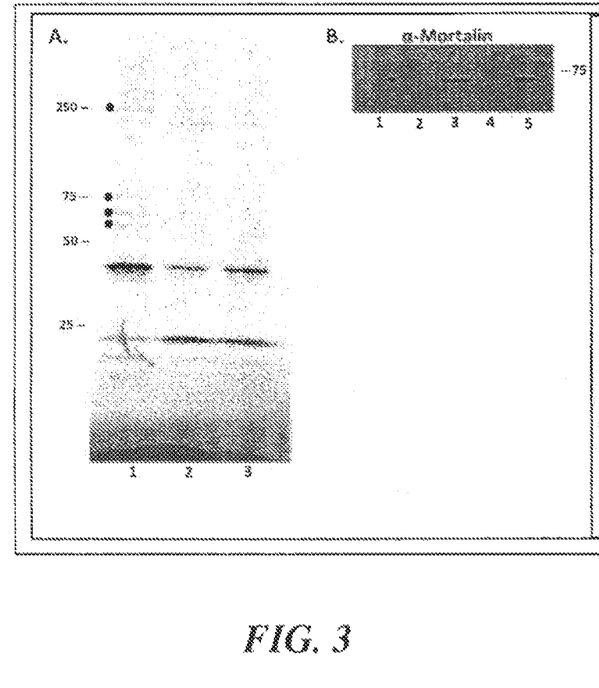

FIG. 1 shows the sequences of synthesized HIV-1 Nef SMRwt peptide having a sequence of VGFPVAAVGF-PVDYKDDDDK (SEQ ID NO: 5), which is the peptide of SEQ ID NO: 3 with a Flag peptide epitope (i.e., DYKDDDDK, SEQ ID NO: 6) at the C-terminal end, and HIV-1 Nef SMRmut peptide (i.e., AGFPVAAAGF-PVDYKDDDDK, SEQ ID NO:7, negative control), as well as the vector constructs expressing either HIV-1 Nef SMRwt peptide fused with GFP, or HIV-1 Nef SMRmut peptide fused with GFP (panel B). As shown in FIG. 2, the SMRwt and SMRmut peptides have no effect on eukaryotic cell growth. Neither peptide cause cell death (data not shown). Using immunoprecipitation with the SMRwt peptide as bait to screen for cellular factors interacting with the SMR domain, a cellular protein Mortalin was co-immunoprecipitated with the SMRwt peptide (FIG. 3). Mortalin, also known as Glucose-regulated protein 75 (GRP75) and Peptide-binding protein 74, is a 679 amino acid long, uninducible member of the heat shock protein 70 family. It has a high degree of identity with other members of the Hsp70 family, including *Escherichia coli* DnaK.

Figure 4:
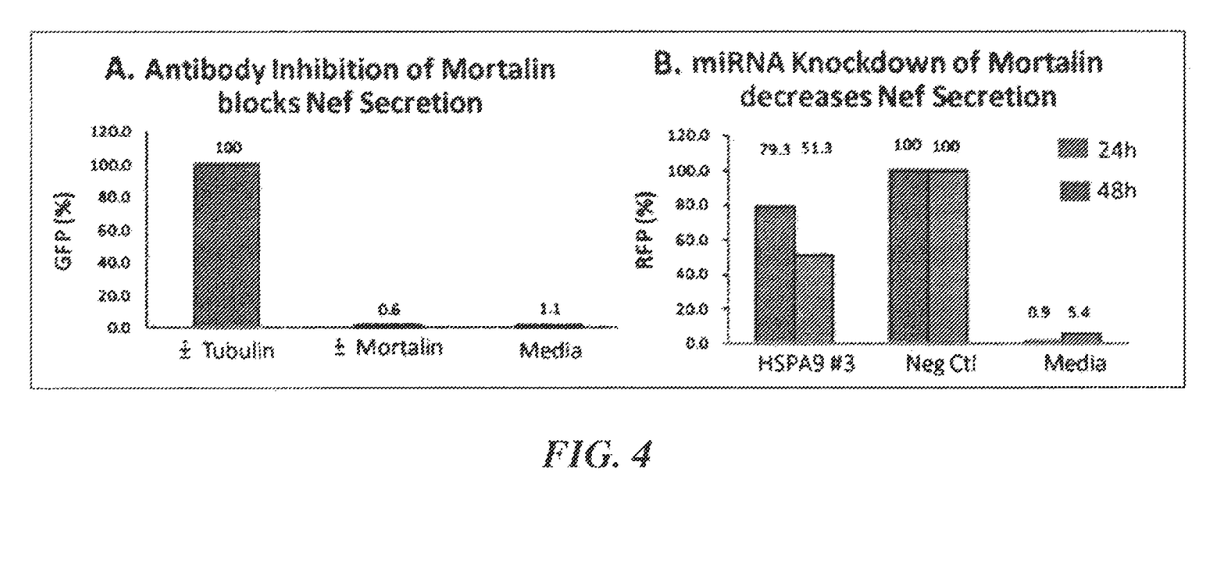
Figure 5:
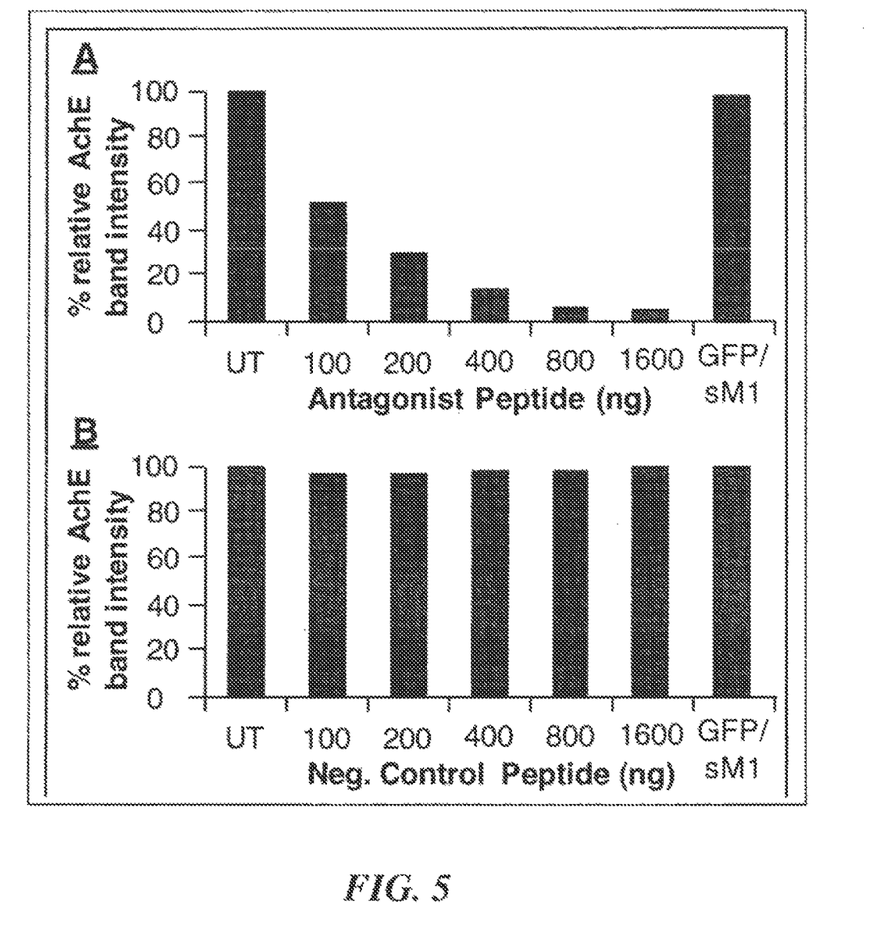

Both antibody and miRNA knockdown experiments (FIG. 4) confirmed that blocking Mortalin in Nef transacted cells blocks Nef-containing exosome secretion, and disrupts Mortalin/Nef interactions which occur through the SMR domain. Thus, the SMRwt peptide directly interacts with Mortalin and disrupts its ability to interact with viral Nef. It was also found that the antimicrobial disrupts non-Nef exosomal secretion driven wholly by the cellular machinery in an examination of its effect on tumor exosome release from several tumor cell lines (FIG. 5).

Based on this structural similarity between Mortalin and DnaK, the SMRwt peptide would likely interact with DnaK, and disrupt function(s) of DnaK. This data suggests that the SMRwt peptide can be a new therapeutic agent that exploits the role of DnaK in secretory and/or growth processes.

EXAMPLE 2

SMRwt Disrupts Growth and Survival of Drug-Resistant Bacteria

Figure 6:
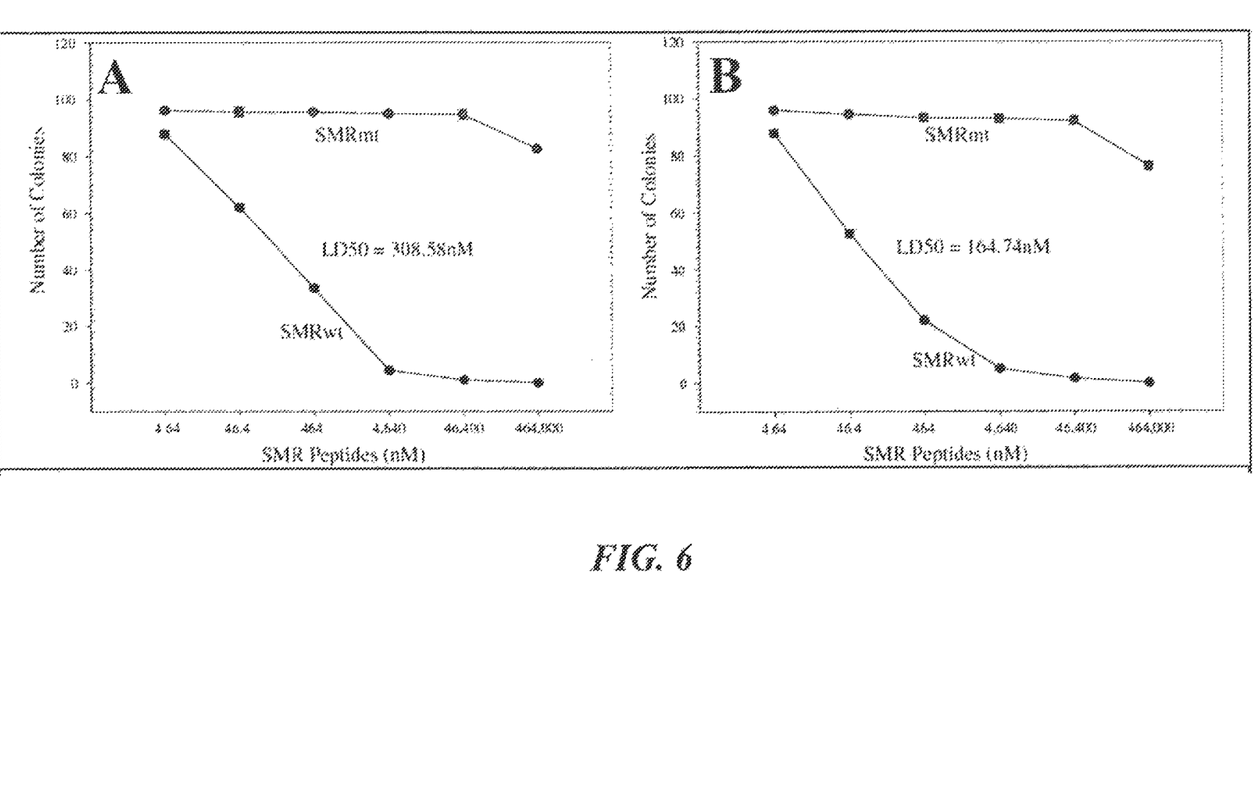

To examine the effects of SMRwt peptide or SMRmut (mutant) peptide on bacterial survival/growth in the presence of drug-resistant bacteria. *E. coli* ($2 \times 10^6$) were transformed with pUC-4K (KAN+) or with pUC18 (AMP+) and grown in the presence of various concentrations (x-axis) of either the antagonist (SMRwt) or the negative control (SMRmut) for 6 hrs (FIG. 6). Briefly, bacterial colonies transformed with pUC18 plasmid containing the ampicillin resistance gene, or pUC4K containing the kanamycin resistance gene were incubated in triplicate at 200-250 rpm at 30° C. The OD at 600 mm was read and adjusted the OD to 0.001 (~$10^6$ cells) by adding LB broth. The bacteria were kept on ice to prevent further growth and change of the OD. 10 microliters of peptide stock (10 μg/μl) was added to 90 μl of diluted bacterial solution (final concentration, 1 mg peptide/ml bacterial suspension) in a sterile 2 ml eppendorf tube. The peptides must be so diluted that the final concentration of DMSO is not more than 5%. The negative control contains 5% DMSO. The tubes were incubated at 30° C. while shaking (200 rpm) for various time periods (0, 1, 3, 6, 12, 24 hours). At each time point, 10 μl of sample from each condition/tube was removed and "dropped" onto the LB agar plate containing suitable antibiotic. Each plate was divided into 4 sections; (i) Negative control—Bacteria exposed to diluent (5% DMSO); (ii) Negative control—Bacteria exposed to diluent without DMSO; (iii) SMRwt—Bacteria exposed to wild type wtSMR peptide antagonist; and (iv) SMRmut—Bacteria exposed to the mutant SMR peptide. Each experiment is performed in triplicate (i.e. on three different plates). After incubating overnight at 30° C., the number of colonies (in each 'drop') on the plate was counted, adjusted for the dilution factor (as above). The results were presented as the number of colonies/ml.

FIG. 6 shows the number of bacteria colonies on LB+KAN (kanamycin) plates (panel A), or LB+AMP (ampicillin) plates (panel B). The data was plotted as a function of peptide dosage. The LD50 (thin dotted line) or MBC50 (minimal bactericidal concentration that kills 50% of the bacteria) is shown for each bacteria/resistance gene.

In the presence of KAN (FIG. 6, panel A) or AMP (FIG. 6, panel B), SMRwt negatively affected bacterial survival after 6 hrs of growth at all SMRwt concentrations tested in a dose-dependent manner. In the presence of KAN or AMP, the MBC50 was about 308.6 nm or 164.7 nm, respectively. In contrast, in the presence of KAN, SMRmut had no effect at SMRmut concentrations up to 150-fold higher than the MBC50 for SMRwt (FIG. 6, panel A). Similarly, in the presence of AMP, SMRmut had virtually no effect at SMRmut concentrations up to 282-fold higher than the MBC50 for SMRwt (FIG. 6, panel B). The antibiotic-dependent differences in MBC50 suggest differences in efficacy for reducing resistance to AMP vs. KAN, which are to be expected given the different modes of action for KAN and AMP.

EXAMPLE 3

SMR wt Affects Bacterial Growth Independent of Drug Resistance

Figure 7:
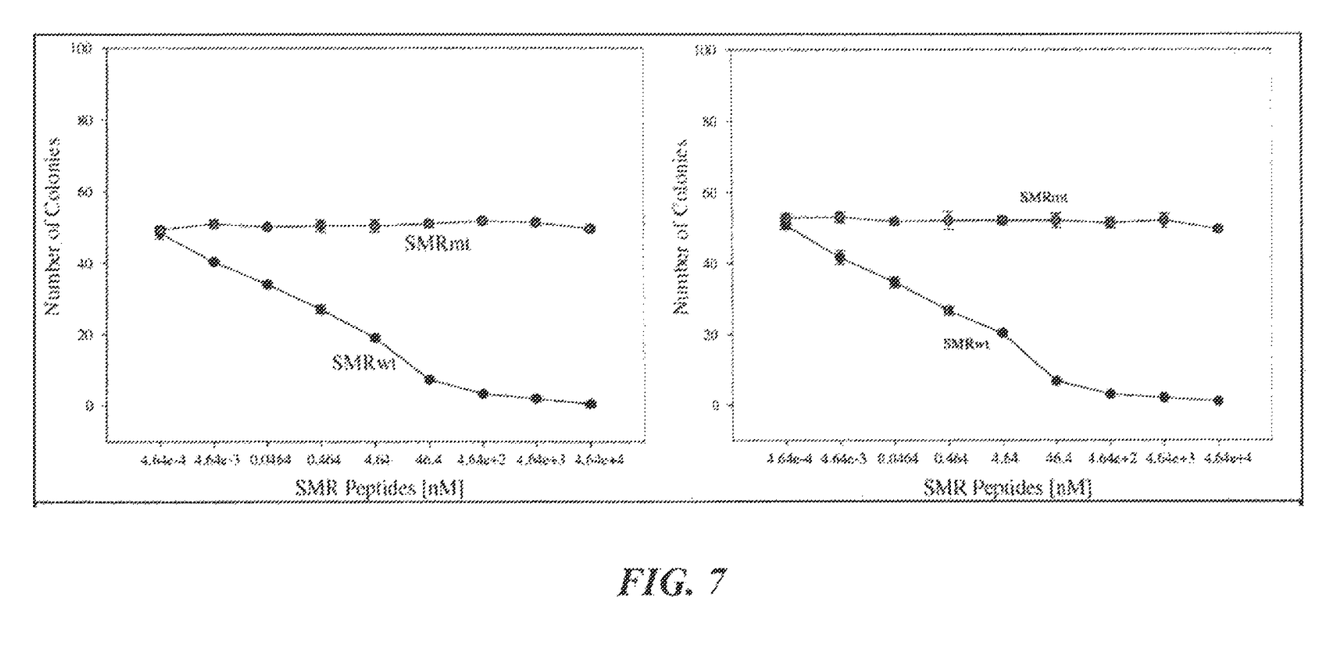

To examine the effects of SMRwt peptide on bacterial survival/growth in the absence of antibiotics, E. coli ($2\times10^6$) transformed with pUC-4K (KAN+) or with pUC18 (AMP+) were grown in the presence of various concentrations (x-axis) of either the antagonist (SMRwt) or the negative control (SMRmut) for 12 hrs (FIG. 7). The resultant pUC-4K (KAN+)-transformed E. coli (panel A) or pUC18 (AMP+)-transformed E. coli bacteria were plated on drug-free LB plates for 12 hours (panel B). Colonies were counted (y-axis) and the data was plotted as a function of peptide dosage in these two non-stressed drug-free environments.

The results in FIG. 7 show that even in these two non-stressful, drug free environments, there was a dose-responsive effect of SMRwt on survival/growth of the cells. The minimum bactericidal concentration (MBC50) for the two plasmid-containing bacteria exposed as described above for 6 hours, and 12 hours are shown in Table 1. As evidenced by the lower MBCs in the antibiotic-free conditions, the SMRwt peptides were significantly more bactericidal under the non-stressed, antibiotic-free conditions.

TABLE 1

| AMPICILLIN/pUC18 | | KANAMYCIN/pUC18 or pUC4-K | |
|---|---|---|---|
| Grown on Ampicillin plates | | Grown on Kanamycin plates | |
| 6 hour exposure | MDC50 = 164.74 nM | 6 hour exposure | MDC50 = 308.58 nM |
| Plated on antibiotic plates | MDC50 = 0.355 μg/ml | Plated on antibiotic plates | MDC50 = 0.865 μg/ml |
| Grown on L-Plates | | Grown on L-Plates | |
| 12 hr exposure | MCD50 = 1.565 nM | 12 hr exposure | MDC50 = 2.03 nM |
| Plated on LB plates | MDC50 = 2.1 ng/ml | Plated on LB plates | MDC50 = 4.75 ng/ml |

EXAMPLE 4

Antibacterial Peptide NEF-SMR Forms a Complex with E. coli DnaK Protein

FIG. 8 shows an immunoprecipitation analysis demonstrating an interaction between SMR interacts and E. coli DnaK. INVITROGEN™ MAX Efficiency® STBL2™ Competent (E. coli) cells were grown overnight at 30° C. in LB Broth without antibiotics and lysed with Novagen® BUGBUSTER™ Protein Extraction Reagent, 1 mg of E. coli lysate was incubated overnight at 4° C. with 20 μL of Sigma® ANTI-FLAG® M2 Affinity Gel in the absence of peptide (lane 2) or in the presence of 1 μg of either the SMRwt (wide-type) peptide (lane 3) or SMRmut (mutant) peptide (lane 4). Following three washes with TBS (50 mM Tris HCl, 150 mM NaCl, pH 7.4), bound proteins/peptides were eluted from the heads by competition with Sigma-Aldrich® 3X FLAG® Peptide.

The elated proteins/peptides were separated by SDS-PAGE and subjected to Western analysts using Abcam® Mouse monoclonal DnaK antibody [8E2/2] (Primary; 1:1000) and Thermo Scientific Immunopure® Goat Anti-Mouse IgG (H+L), Peroxidase Conjugated antibody (Secondary; 1:2000). The results of this analysis show that the SMRwt peptide forms a complex with the DnaK protein, while the negative control peptide exhibits negligible binding.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method of treating a microbial infection of gram positive bacteria, comprising:
   administering to a subject in need thereof an effective amount of an antimicrobial peptide comprising an antimicrobial domain comprising the amino acid sequence of SEQ ID NO: 3 or SEQ ID NO: 5.

2. The method of claim 1, wherein said antimicrobial peptide further comprises a cell penetrating peptide (CPP) domain.

3. The method of claim 1, wherein said antimicrobial peptide further comprises a targeting domain.

4. The method of claim 1, wherein said antimicrobial peptide is a PEGylated peptide.

5. A method of treating a microbial infection of gram positive bacteria, comprising:
   administering to a subject in need of such treatment an effective amount of an expression vector capable of expressing an antimicrobial peptide comprising the amino acid sequence of SEQ ID NO: 3 or SEQ ID NO: 5.

6. The method of claim 5, wherein said expression vector is a plasmid expression vector.

7. The method of claim 5, wherein said expression vector is a viral expression vector.

8. The method of claim 5, wherein said expression vector is a bacteria phage displaying said antimicrobial peptide on its surface.

9. The method of claim 1, wherein said antimicrobial peptide comprises the amino acid sequence of SEQ ID NO: 3.

10. The method of claim 1, wherein said antimicrobial peptide comprises the amino acid sequence of SEQ ID NO: 5.

* * * * *

SEQUENCE LISTING

<160> NUMBER OF SEQ ID NOS: 7

<210> SEQ ID NO 1
<211> LENGTH: 5
<212> TYPE: PRT
<213> ORGANISM: Human immunodeficiency virus

<400> SEQUENCE: 1

Val Gly Phe Pro Val
1               5

<210> SEQ ID NO 2
<211> LENGTH: 5
<212> TYPE: PRT
<213> ORGANISM: Simian immunodeficiency virus

<400> SEQUENCE: 2

Val Gly Val Ser Val
1               5

<210> SEQ ID NO 3
<211> LENGTH: 12
<212> TYPE: PRT
<213> ORGANISM: Human immunodeficiency virus

<400> SEQUENCE: 3

Val Gly Phe Pro Val Ala Ala Val Gly Phe Pro Val
1               5                   10

<210> SEQ ID NO 4
<211> LENGTH: 12
<212> TYPE: PRT
<213> ORGANISM: ARTIFICIAL SEQUENCE
<220> FEATURE:
<223> OTHER INFORMATION: Synthetic

<400> SEQUENCE: 4

Val Gly Val Ser Val Ala Ala Val Gly Val Ser Val
1               5                   10

<210> SEQ ID NO 5
<211> LENGTH: 20
<212> TYPE: PRT
<213> ORGANISM: ARTIFICIAL SEQUENCE
<220> FEATURE:
<223> OTHER INFORMATION: Synthetic

<400> SEQUENCE: 5

Val Gly Phe Pro Val Ala Ala Val Gly Phe Pro Val Asp Tyr Lys Asp
1               5                   10                  15

Asp Asp Asp Lys
            20

<210> SEQ ID NO 6
<211> LENGTH: 8
<212> TYPE: PRT
<213> ORGANISM: ARTIFICIAL SEQUENCE
<220> FEATURE:
<223> OTHER INFORMATION: Synthetic

<400> SEQUENCE: 6

Asp Tyr Lys Asp Asp Asp Asp Lys
1               5

<210> SEQ ID NO 7

```
<211> LENGTH: 20
<212> TYPE: PRT
<213> ORGANISM: ARTIFICIAL SEQUENCE
<220> FEATURE:
<223> OTHER INFORMATION: Synthetic

<400> SEQUENCE: 7

Ala Gly Phe Pro Val Ala Ala Ala Gly Phe Pro Val Asp Tyr Lys Asp
1               5                   10                  15

Asp Asp Asp Lys
            20
```